(12) United States Patent
Kraus

(10) Patent No.: US 6,641,564 B1
(45) Date of Patent: Nov. 4, 2003

(54) SAFETY INTRODUCER APPARATUS AND METHOD THEREFOR

(75) Inventor: Mark C. Kraus, Independence, MN (US)

(73) Assignee: MedAmicus, Inc., Minneapolis, MN (US)

(*) Notice: Subject to any disclaimer, the term of this patent is extended or adjusted under 35 U.S.C. 154(b) by 196 days.

(21) Appl. No.: 09/707,162

(22) Filed: Nov. 6, 2000

(51) Int. Cl.[7] ............................................. A61M 5/178
(52) U.S. Cl. ............... 604/164.1; 604/110; 604/164.01; 604/164.05; 604/165.01; 604/160; 604/167.01; 604/167.04; 604/168.01; 606/185
(58) Field of Search ..................... 604/164.1, 164.01, 604/164.09, 165.01, 165.02, 167.06, 167.04, 168.01, 171, 164.05, 160, 110, 104; 606/167, 185

(56) References Cited

U.S. PATENT DOCUMENTS

| 3,630,192 A | * | 12/1971 | Jamshidi ..................... 600/567 |
| 4,046,144 A | * | 9/1977 | McFarlane ................ 604/168.01 |
| 4,230,123 A | * | 10/1980 | Hawkins, Jr. .............. 604/165.02 |
| 4,488,545 A | * | 12/1984 | Shen ........................ 604/165.02 |
| RE31,855 E | * | 3/1985 | Osborne .................. 604/164.05 |
| 4,531,937 A | | 7/1985 | Yates .......................... 604/53 |
| 4,629,450 A | * | 12/1986 | Suzuki et al. ............... 604/164 |
| 4,772,266 A | * | 9/1988 | Groshong ................ 604/164.05 |
| 4,907,598 A | * | 3/1990 | Bauer ......................... 600/566 |
| 4,944,728 A | * | 7/1990 | Carrell et al. ............. 604/164.08 |
| 4,978,334 A | * | 12/1990 | Toye et al. ................... 604/51 |
| 4,994,034 A | * | 2/1991 | Botich et al. ................ 604/110 |
| 4,995,866 A | * | 2/1991 | Amplatz et al. .............. 604/53 |
| 5,057,083 A | * | 10/1991 | Gellman ..................... 604/164 |
| 5,098,392 A | * | 3/1992 | Fleischhacker et al. 604/164.05 |
| 5,169,387 A | * | 12/1992 | Kronner .................. 604/164.06 |
| 5,188,599 A | * | 2/1993 | Botich et al. ................ 604/110 |
| 5,190,528 A | * | 3/1993 | Fonger et al. ............... 604/171 |
| 5,295,974 A | * | 3/1994 | O'Laughlin ................. 604/171 |
| 5,407,431 A | * | 4/1995 | Botich et al. ................ 604/110 |
| 5,409,469 A | * | 4/1995 | Schaerf ...................... 604/160 |

(List continued on next page.)

FOREIGN PATENT DOCUMENTS

| EP | 0232994 | * | 8/1987 | .......... A61M/25/00 |
| WO | 98/24494 | * | 6/1998 | ............ A61M/5/00 |
| WO | 00/06221 | * | 2/2000 | ............ A61M/5/00 |

Primary Examiner—Rodney M. Lindsey
(74) Attorney, Agent, or Firm—Schwegman, Lundberg, Woessner & Kluth, P.A.

(57) ABSTRACT

An introducing apparatus is provided which includes an elongate tubular sheath extending from a sheath proximal end to a sheath distal end. The sheath has a bore sized to receive a dilator therethrough. The sheath further includes at least one tab extending away from a longitudinal axis of the sheath. The dilator extends from a dilator proximal end to a dilator distal end. The introducing apparatus further includes a needle disposed within the dilator, and retractably coupled with the dilator. A distal end of the needle is flexible.

30 Claims, 10 Drawing Sheets

U.S. PATENT DOCUMENTS

| | | | | |
|---|---|---|---|---|
| 5,454,790 A | * | 10/1995 | Dubrul | 604/104 |
| 5,531,694 A | | 7/1996 | Clemens et al. | 604/110 |
| 5,575,777 A | | 11/1996 | Cover et al. | 604/198 |
| 5,616,135 A | | 4/1997 | Thorne et al. | 604/192 |
| 5,685,855 A | | 11/1997 | Erskine | 604/168 |
| 5,685,863 A | | 11/1997 | Botich et al. | 604/198 |
| 5,702,367 A | * | 12/1997 | Cover et al. | 604/110 |
| 5,741,233 A | * | 4/1998 | Riddle et al. | 604/165.01 |
| 5,755,693 A | * | 5/1998 | Walker et al. | 604/160 |
| 5,766,135 A | * | 6/1998 | Terwilliger | 600/567 |
| 5,797,880 A | * | 8/1998 | Erskine | 604/110 |
| 5,851,212 A | * | 12/1998 | Zirps et al. | 606/167 |
| 5,873,854 A | * | 2/1999 | Wolvek | 604/104 |
| 5,964,740 A | * | 10/1999 | Ouchi | 606/185 |
| 5,989,220 A | * | 11/1999 | Shaw et al. | 604/110 |
| 6,016,595 A | | 1/2000 | Dysarz | 29/423 |
| 6,077,244 A | * | 6/2000 | Botich et al. | 604/110 |
| 6,096,005 A | * | 8/2000 | Botich et al. | 604/110 |
| 6,102,894 A | | 8/2000 | Dysarz | 604/110 |
| 6,120,494 A | * | 9/2000 | Jonkman | 604/506 |
| 6,156,010 A | * | 12/2000 | Kuracina et al. | 604/168.01 |
| 6,379,337 B1 | | 4/2002 | Mohammad M. B. B. S. | 604/195 |
| 6,379,338 B1 | | 4/2002 | Garvin | 604/195 |
| 6,398,743 B1 | | 6/2002 | Halseth et al. | 600/585 |
| 2002/0045843 A1 | * | 4/2002 | Barker et al. | 604/110 |
| 2003/0032922 A1 | * | 2/2003 | Moorehead | 640/110 |

* cited by examiner

SAFETY INTRODUCER APPARATUS AND METHOD THEREFOR

TECHNICAL FIELD

The present invention generally relates to introducers and introducing assemblies. Specifically, it relates to a safety introducer with a safety needle.

BACKGROUND

Introducer devices provide for access to the venous system and are employed for inserting medical devices such as catheters, guidewires, leads, infusion ports, dialysis ports, dialysis catheters, and others. A typical procedure for gaining access to the central venous system or the arterial system with an introducer is the Seldinger Introduction Method. The Seldinger Method provides for insertion of a needle into the vasculature of a patient. Once the needle is in the vessel, the physician aspirates the needle to assure that the needle is in the vessel, and to draw out air present in the bore of the needle. The syringe is removed and discarded. A guide wire is inserted through the needle, and the needle is removed over the guide wire. The introducer, which includes a dilator and the sheath, is placed over the guidewire and inserted into the vessel. With the introducer and wire guide in the vessel, the dilator and wire guide are removed leaving only the sheath in the vessel. The desired medical device is implanted through the bore of the sheath. The sheath is optionally removed from the medical device.

Any time a needle is used it can cause transmission of various pathogens, most notably the Human Inmune Virus (HIV), due to an accidental needle stick of an uninfected person after the needle is withdrawn from the patient, or due to re-use of a needle. Furthermore, the Seldinger Method requires numerous steps, resulting in extra costs, potential trauma, and/or pain for a patient.

Accordingly, what is needed is an introducer and dilator which can eliminate needle re-use or inadvertent needle sticks. What is also needed is an introducer assembly which does not distract or interfere with the implantation process.

SUMMARY

An introducing apparatus is provided which includes an elongate tubular sheath extending from a sheath proximal end to a sheath distal end. The sheath has a bore sized to receive a dilator therethrough, and a bore sized to receive medical instruments therethrough. The dilator extends from a dilator proximal end to a dilator distal end. The introducing apparatus further includes a needle disposed within the dilator, where the needle is retractably coupled with the dilator with a needle retraction mechanism. The needle extends from a needle proximal end to a needle distal end and has an intermediate portion therebetween. The distal end of the needle extends out of the dilator distal end in a first position, and the needle distal end is retracted within the dilator distal end in a second position. At least a portion of the needle is flexible. The needle distal end is optionally echogenic.

Several options for the introducing apparatus are as follows. For example, in one option, the sheath is separable without damage to an instrument inserted therethrough. In another option, the needle distal end is more flexible than the dilator. In yet another option, the needle distal end has the same or less of flexibility as the dilator. A portion of the intermediate portion and the needle distal end are more flexible than the dilator in another option. In another option, the intermediate portion of the needle is a flexible coil. In yet another option, the intermediate portion and the needle distal end are flexible, and the needle is formed of a unitary structure of nitinol.

Further options include an air permeable filter and/or a valve coupled with the sheath. In another option, the dilator includes a catch sized and shaped to prevent re-extension of the needle. In yet another option, the introducing apparatus includes a locking mechanism configured to temporarily lock the sheath with the dilator. The dilator, in another option, further includes a blood flashback chamber. In one option, the intermediate portion of the dilator is further defined by first and second dilator intermediate portions, and the dilator first intermediate portion has a greater outer diameter than an outer diameter of the dilator distal end, and the dilator second intermediate portion has a greater outer diameter than the outer diameter of the first intermediate portion.

In another embodiment, an introducing apparatus is provided which includes an elongate tubular sheath extending from a sheath proximal end to a sheath distal end. The sheath has a bore sized to receive a dilator therethrough. The sheath further includes at least one tab extending away from a longitudinal axis of the sheath. The dilator extends from a dilator proximal end to a dilator distal end. The introducing apparatus further includes a needle disposed within the dilator. The needle extends from a needle proximal end to a needle distal end and has an intermediate portion therebetween. At least a portion of the needle is flexible. The needle distal end is optionally echogenic.

Several options for the introducing apparatus are as follows. For example, in one option, the sheath is separable without damage to an instrument inserted therethrough. In another option, the needle distal end is more flexible than the dilator. In yet another option, the needle distal end has the same or less of flexibility as the dilator.

Further options include a valve coupled with the sheath. In another option, the dilator includes a catch sized and shaped to prevent re-extension of the needle. In yet another option, the introducing apparatus includes a locking mechanism configured to temporarily lock the sheath with the dilator. The dilator, in another option, further includes a blood flashback chamber and a gas permeable filter. In one option, the intermediate portion of the dilator is further defined by first and second dilator intermediate portions, and the dilator first intermediate portion has a greater outer diameter than an outer diameter of the dilator distal end, and the dilator second intermediate portion has a greater outer diameter than the outer diameter of the first intermediate portion.

A method is provided which includes disposing a needle within a dilator, where at least a portion of the needle is more flexible than the dilator. The method further includes retractably coupling a needle with a dilator, the dilator extending to a dilator distal end, where the needle extends to a needle distal end and the needle distal end extends beyond the dilator distal end. The method further includes disposing the needle and dilator within a sheath to form an introducing apparatus, and inserting the introducing apparatus into a body.

Several options for the method are as follows. For example, in one option, the method further includes retracting the needle within the dilator, and removing the needle and the dilator from the sheath. In another option, the method further includes preventing re-extension of the needle from the dilator. In yet another option, the method further includes removing the dilator and needle from the sheath, inserting an instrument through the sheath, and separating the sheath from the instrument without damage to the instrument. A valve is coupled with the sheath in another option.

The introducing apparatus beneficially provides a safety introducer, which allows for the needle to be safely retracted within the dilator after its use, and optionally prevents re-use of the same needle, for example on another patient.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
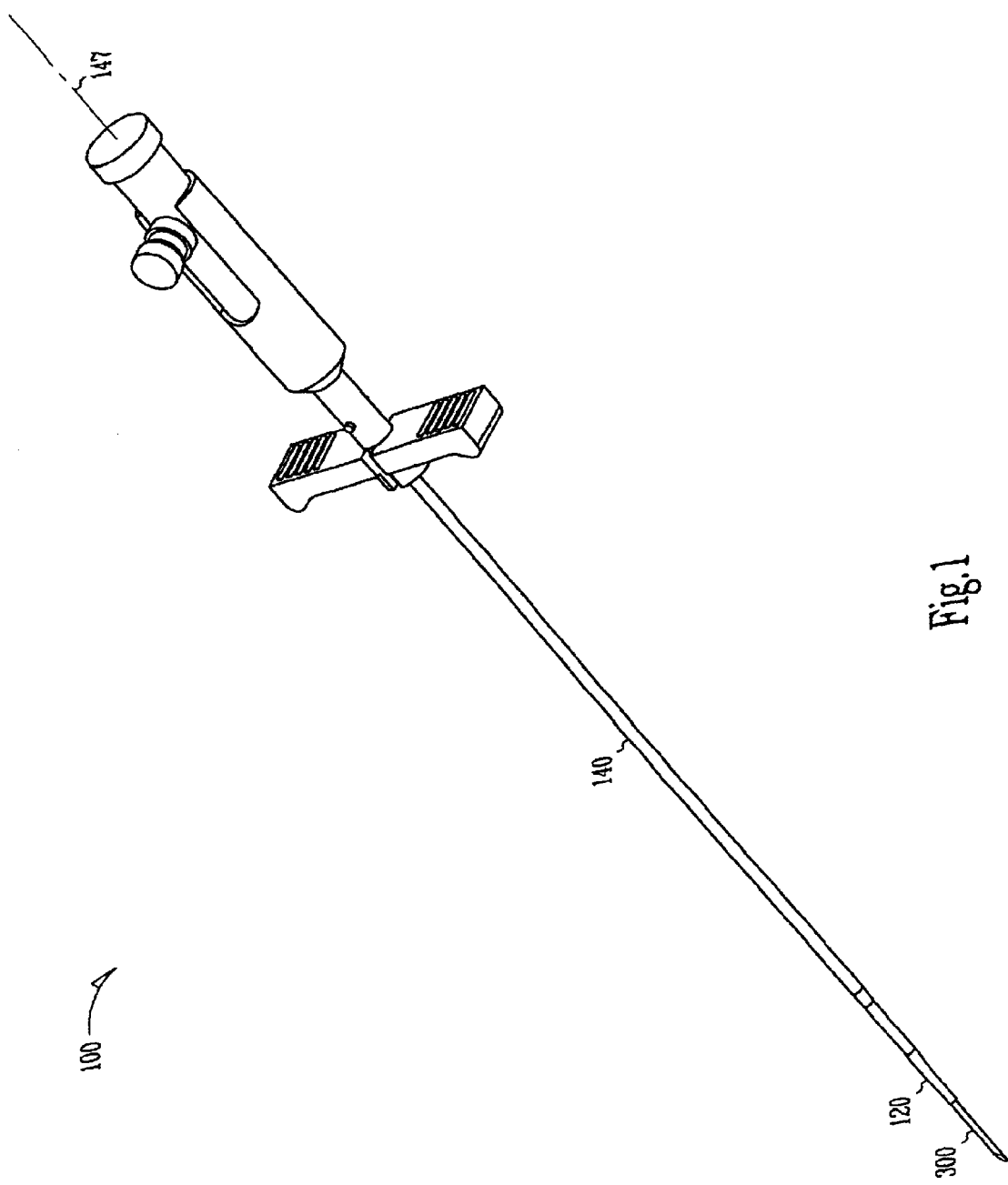
FIG. 1 illustrates a perspective view of an introducing apparatus as constructed in accordance with one embodiment.
Figure 2:
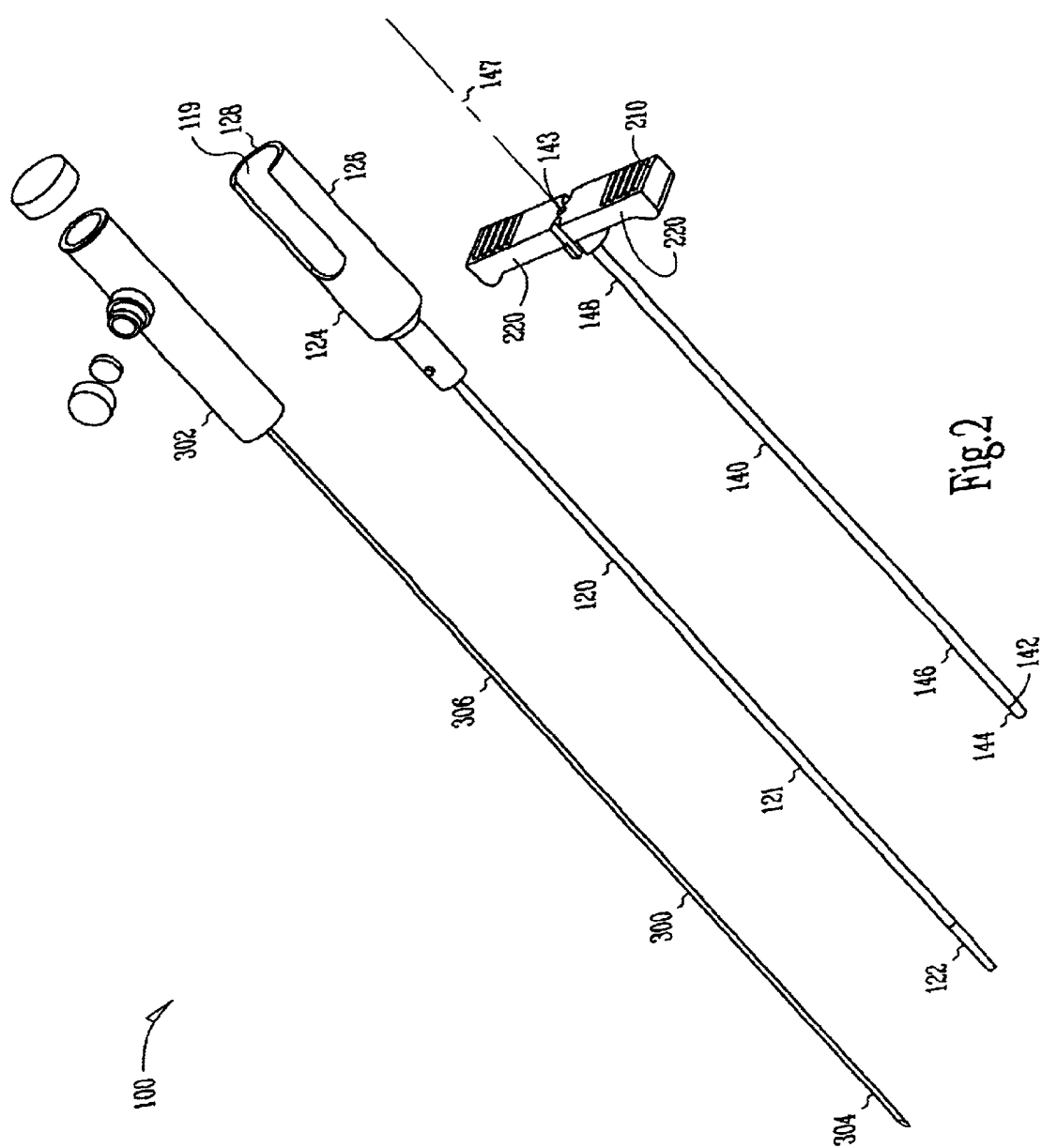
FIG. 2 illustrates a perspective view of a disassembled introducing apparatus as constructed in accordance with one embodiment.

An introducer assembly 100, as shown in FIGS. 1 and 2, includes generally a sheath 140 and a dilator 120 through the sheath 140, and a needle 300 disposed within the dilator 120. The dilator 120 and the needle 300 allow for the introducer assembly 100 to be introduced into a vessel of a patient. The dilator 120 extends from a dilator distal end 122 to a dilator proximal end 124, where the dilator distal end 122 is insertable into a patient. Disposed between the dilator distal end 122 and the dilator proximal end 124 is a dilator intermediate portion 121. The dilator distal end 122 optionally ends in a tapered end 123, as shown in more detail in FIGS. 3A and 3B. In another option, the dilator distal end 122 has a tapered end 123, and a second tapered portion 125, where the second tapered portion 125 is disposed in the dilator intermediate portion 121. In one option, an outer surface 336 of the needle 300 directly abuts an inner surface 118 of the dilator, thereby allowing the introducing assembly 100 to have a thin outer diameter.

Figure 8:
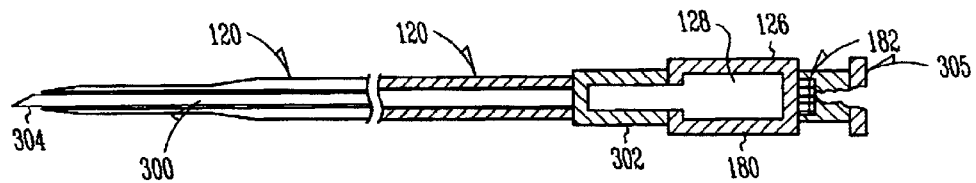
FIG. 8 illustrates a cross-sectional view of a dilator and needle assembly as constructed in accordance with one embodiment.

Referring again to FIGS. 1 and 2, at the dilator proximal end 124 is a hub 126 having a bore 128 therethrough. The dilator 120 also includes a passage 119 therethrough, aligned with the bore 128, which allows the dilator 120 to be inserted over the sheath 140. In a further option, the dilator 120 includes a blood flashback chamber 180, which is coupled with the hub 126 of the dilator 120, as shown in more detail in FIG. 8 The blood flashback chamber 180 is filled with blood as the physician inserts the needle 300 of the introducer assembly 100 within a vessel of a patient. One end of the flashback chamber 180 is sealed by a gas permeable filter 182 which allows air to pass therethrough, although prevents blood to pass from the flashback chamber 180.

During use of the assembly 100 (FIG. 1), once the needle has entered a blood pressure environment, the pressure will cause the blood to exit the hole in the blood vessel made by the needle 300. The blood enters a distal end 304 of the needle 300, and travels through the passage 143 of the sheath 140, which has a lower pressure than blood pressure. The blood will travel from the distal end 304 of the needle 300 to the proximal end 302 of the needle 300 and into the flashback chamber 180 located at the proximal end 302 of the needle 300. The blood pressure, which is greater than the ambient pressure outside of the blood vessel, will force the air in the needle 300 out of the gas permeable filter 182 coupled with the flashback chamber 180.

The gas permeable filter 180 is in contact with the ambient environment outside of the needle 300, to which the air escapes. Once all of the air has been pushed out of the needle 300 by the blood pressure, the blood appears in the flashback chamber 180. The filter 180 prevents blood from exiting the chamber 180. The flashback chamber 180 is visible to the user, indicating to the user that the needle 300 has been aspirated, and that access to the blood vessel has been obtained. In another option, the flashback chamber 180 further includes a luer fitting 305. The user optionally attaches a syringe to the luer fitting 305, and aspirates the needle 300 using the syringe.

The dilator 120 is sized to be received by the sheath 140 therein. The sheath 140 allows for additional instruments to be inserted therethrough and inserted into the patient. The sheath 140 includes various types of sheaths, for instance, the sheath 140 can comprise a sheath which has a strengthening braid of material. Alternatively, the sheath 140 includes those which are modified to prevent bends in the elongate sheath. The sheath 140 is defined in part by a longitudinal axis 147, and the sheath 140 extends from a sheath distal end 142 to a sheath proximal end 148. The sheath 140 is coaxial with the dilator 120, and optionally the needle 300, where they each share the same longitudinal axis 147. The distal end 142 of the sheath 140 is first inserted into the patient and the proximal end 148 remains outside of the patient. Near the distal end 142 is an optional tapered portion 144 which provides a transition to a cylindrical portion 146. The sheath 140 also includes a passage 143 therethrough, where the passage 143 is substantially aligned with the longitudinal axis 147 of the sheath 140. The passage 143 allows for the introduction of the dilator 120 therethrough. After the introducer assembly 100 has been inserted into a patient, and the dilator 120 is removed, other medical instruments can be easily inserted into and through the sheath 140, and introduced into the patient.

Figure 5:
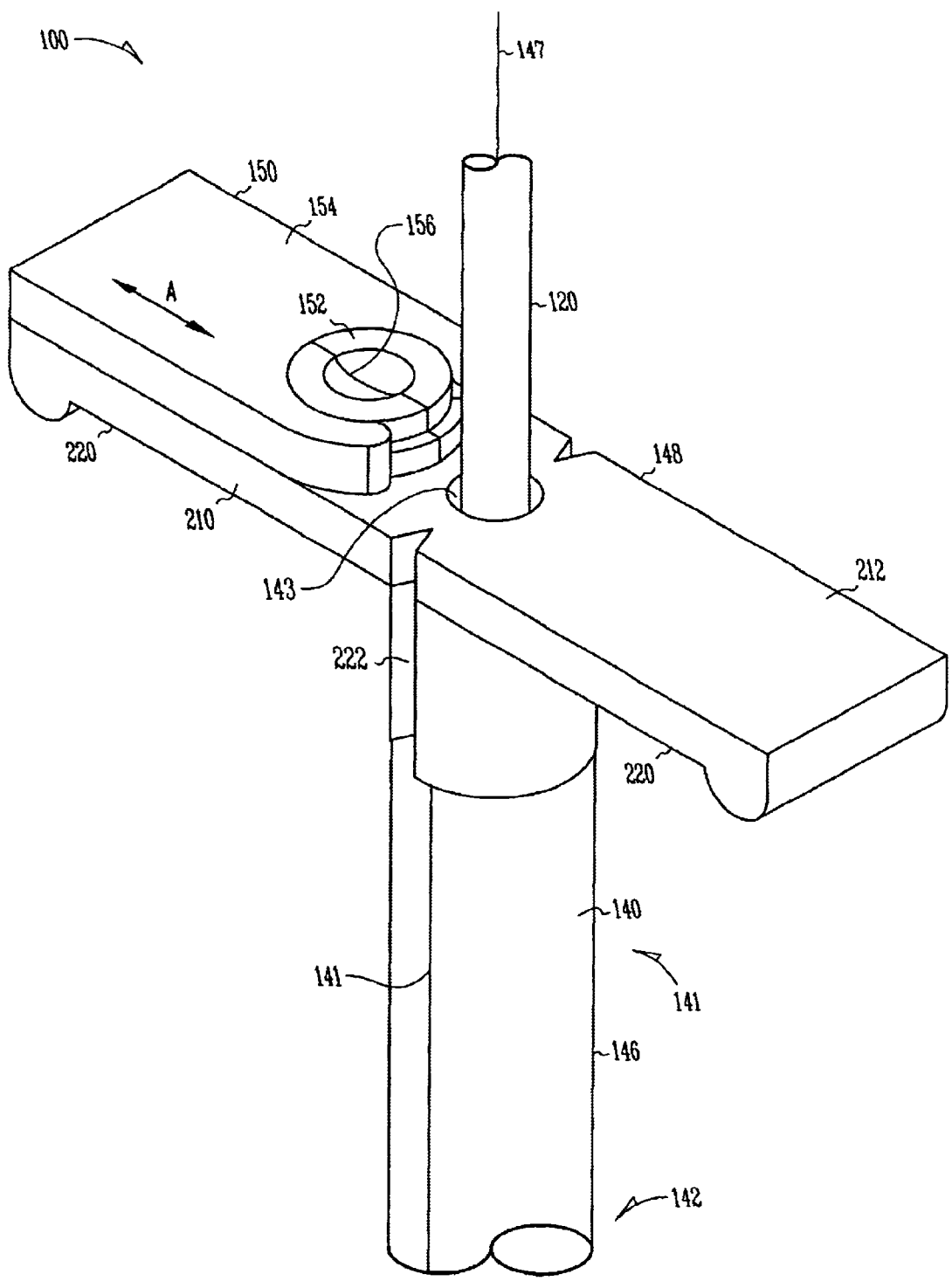
FIG. 5 illustrates a perspective view of a portion of an introducing apparatus as constructed in accordance with one embodiment.

The sheath 140 includes at least one tab 210 which extends radially outward from the sheath 140. In one embodiment, the sheath 140 includes two tabs 220 which are disposed 180 degrees from each other. Optionally, tab break lines 222 (FIG. 5) are disposed between along the sheath 140, for instance between the two tabs 220 are tab break lines 222 (FIG. 5).

In another option, the sheath 140 is splittable such that the sheath 140 is separable into two or more components. The sheath 140 is separable or splittable away from instruments inserted therethrough which prevents disruption to or removal of instruments or devices which have been inserted through the sheath 140. The splittable sheath 140 is separable from the instruments inserted therethrough, where no damage occurs to the instruments during the removal of the sheath 140. For example, in one option, the sheath 140 includes at least one score line 141, as shown in FIG. 5. The sheath 140 is externally scored, and optionally two scores 141 are 180 degrees from each other. The scores 141 are aligned with the optional tab break lines 222 such that the tab break lines 222 and the scores 141 are disposed between the two tabs 220. Alternatively, the sheath 140 is splittable using a slitting device, a rip cord or strengthening strip running along the longitudinal length of the sheath, a weakening which allows the introducer to be ripped apart, or other techniques which allow the sheath 140 to separate without damage to an instrument inserted therethrough, or without disruption to the procedure.

Figure 9:
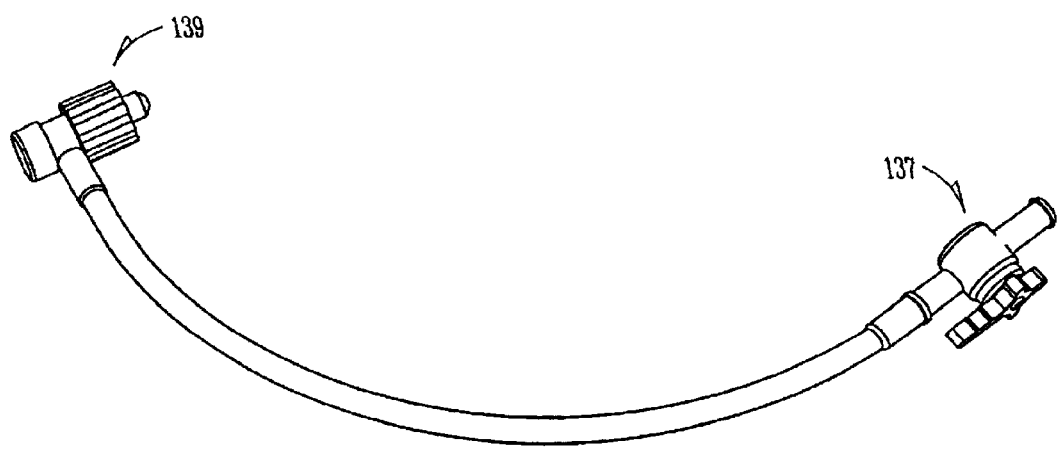
FIG. 9 illustrates a valve and stop cock assembly for use in arterial applications.

It should be noted that the introducer assembly 100 can be used for both venous and arterial applications. For arterial applications, it may not be necessary to remove the sheath while a medical instrument is inserted therethrough. In one option, the sheath 140 is not separable. FIG. 9 illustrates an example of a valve 139 to be used with the introducer assembly 100, for example, for arterial applications. The introducer 100 is disposed through the valve 139, and the valve 139 is coupled with a proximal end 148 of the sheath 140. In a further option, a stop cock 137 is coupled with the valve 139. The stop cock 137 allows for the introduction of fluids therethrough and into the patient.

Referring again to FIGS. 1 and 2, as mentioned above, a needle 300 is disposed within the dilator 120. In one option, the needle is retractably coupled with the dilator. The needle 300 extends from a needle proximal end 302 to a needle distal end 304, and includes a needle intermediate portion 306 therebetween. The needle 300 is coaxial with the sheath 140 and the dilator 120 (FIG. 1). For instance, a longitudinal axis of the needle 300 is aligned with the longitudinal axis 147 of the sheath 140 (FIG. 1), when the needle 300 is in the extended and retracted positions.

Figure 3A:
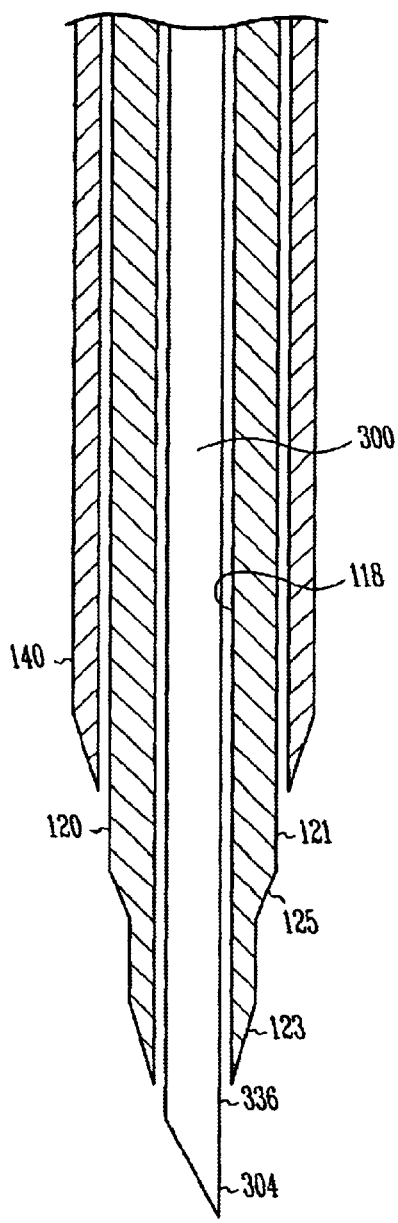
FIG. 3A illustrates side cross-sectional view of a portion of an introducing apparatus as constructed in accordance with one embodiment.
Figure 3B:
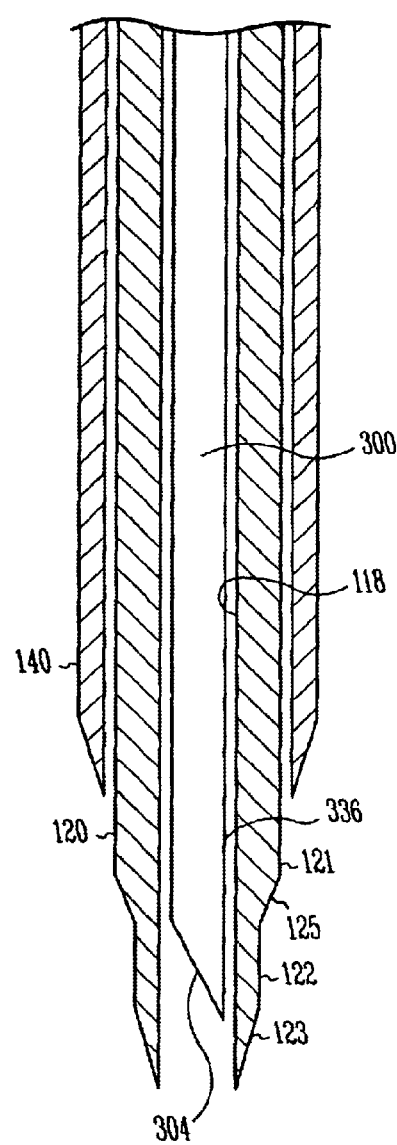
FIG. 3B illustrates side cross-sectional view of a portion of an introducing apparatus as constructed in accordance with one embodiment.

In one option, the needle distal end 304 is echogenic, which allows for the physician to view the needle 300 during the process of implanting the medical device. The needle 300 is movably disposed within the dilator 120, as shown in FIGS. 3A and 3B. The distal end 304 of the needle extends out from the dilator distal end 122 in a first position (FIG. 3A). The needle distal end 304 is retracted within the dilator 120 in a second position (FIG. 3B), and the needle 300 is retractably coupled with the dilator.

Figure 13:
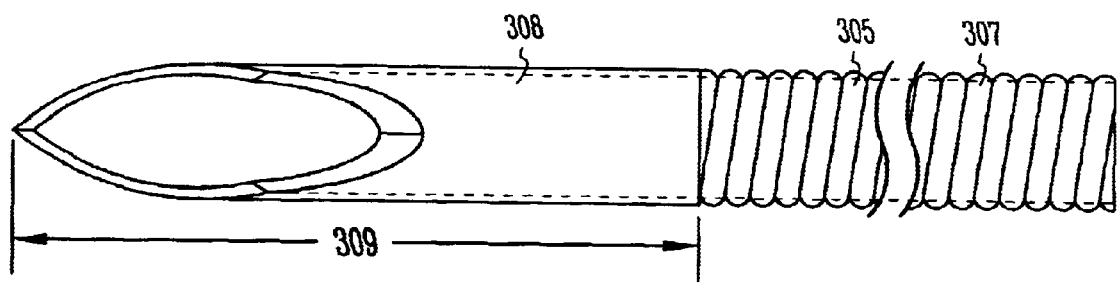
FIG. 13 illustrates a side elevational view of a needle as constructed in accordance with another embodiment.

The needle 300, in one option, is flexible along a portion of or the entire needle, allowing the needle to be inserted further into a vessel than conventional needles. For example, the needle 300 is formed of flexible material, such as nitinol. In one option, the needle 300 is formed of a unitary structure of nitinol. In another option, at least a portion of the needle 300 is flexible. For instance, a portion of the needle 300 is formed of a flexible material such as nitinol. In another option, at least a portion of the needle 300 is flexible as it includes a first portion 310 formed of a spring coil 307, as shown in FIG. 13. In yet another option, the spring coil 307 is coated with a material, such as Teflon. Other coatings which maintain flexibility of the needle 300 are suitable as well. In yet a further option, a second portion 308 of rigid or semi-rigid material is coupled with the spring coil 307. The second portion 308, in one option, has a length 309 of about 0.5 inches.

Since the needle is flexible, the guidewire is no longer necessary to introduce devices into a patient. This allows for the assembly to be manufactured more cost effectively, and further allows for a faster introduction process. In another option, only the needle distal end 304 and/or the needle intermediate portion 306 is flexible. Optionally, the needle 300 has the same or more flexibility than the dilator 120. The needle 300 is flexible enough to permit insertion of the needle 300 through the right side subclavian vein into the superior venacava without kinking or causing the dilator to perforate the vein. In another option, the needle 300 is flexible enough such that it is insertable around the aortic bifurcation without kinking or causing the dilator to perforate a femoral artery. In a further option, the needle 300 is flexible enough such that it can be bent into a circle having a 0.5 inch radius. In addition, the needle 300 has sufficient flexibility and column strength to be pushed through the vasculature by a user without kinking the needle 300.

Figure 10:
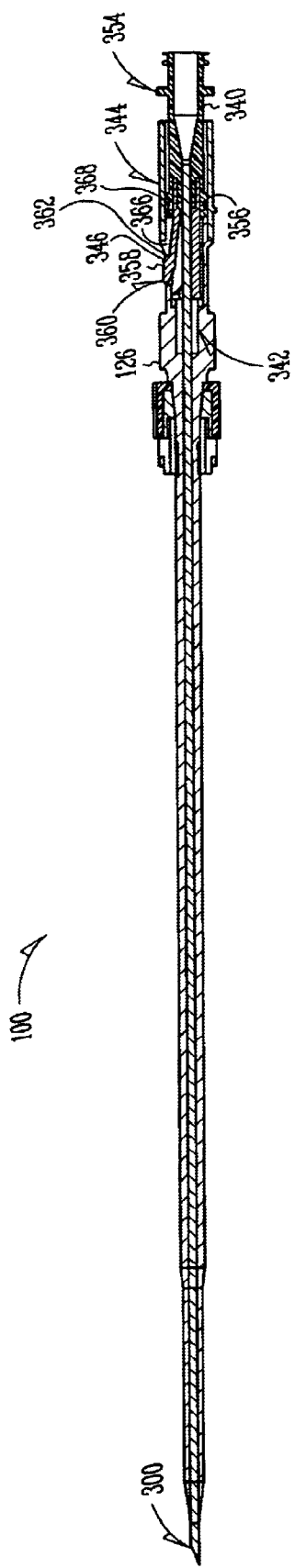
FIG. 10 illustrates a cross-sectional view taken along A—A of FIG. 11, of the introducer apparatus as constructed in accordance with one embodiment.
Figure 11:
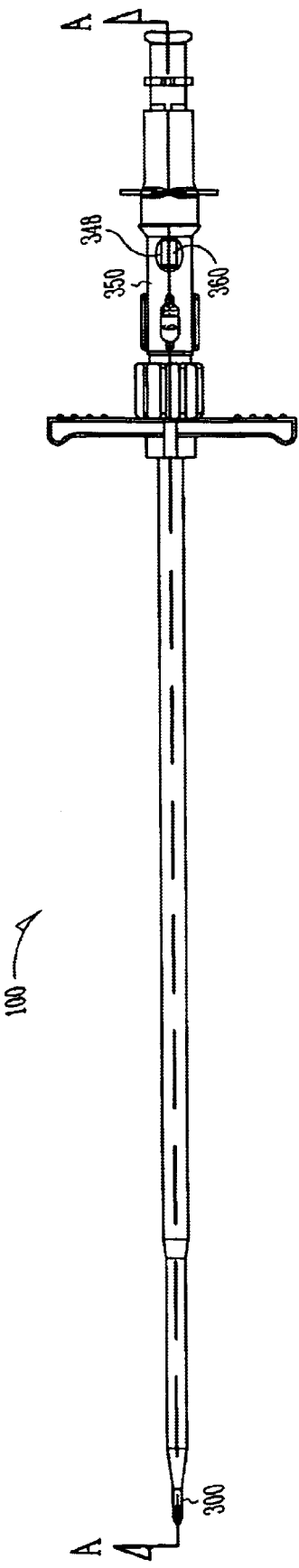
FIG. 11 illustrates a side elevational view of an introducer apparatus as constructed in accordance with one embodiment.

FIGS. 10 and 11 illustrate the needle 300, the sheath 140 and the dilator 120 in greater detail. The needle 300 is attached to a needle hub 340, which is retractably coupled with the dilator 120. A rear barrel 344 is coupled with the dilator 120, where the rear barrel 344 does not move relative to the dilator 120. A bias member 342, such as a spring, is disposed within the hub 126 of the dilator 120, and biases the needle hub 340 and the needle 300 toward the proximal end of the assembly 100 toward a retracted position. A needle retainer 346 releasably retains the needle hub 340 against the bias of the bias member 342.

The rear barrel 344 has a hollow central bore, and includes at least one locking aperture 348 in a sidewall 350 of the rear barrel 344. The proximal end 352 of the rear barrel 344 is generally open for receiving the needle hub 340 and a connector hub 354 therein, where the connector hub 354 in one option comprises a luer fitting. The rearel 344 further includes a stop 356 which limits displacement of the needle 300, and limits the retraction of the needle 300.

The needle hub 340 is generally cylindrical and is coupled with the needle 300. The needle retainer 346 includes an actuator 358. In one option, the actuator 358 comprises a deforinable arm. Coupled with at least a portion of an actuator 358 is an actuator button 360. The actuator button 360 is received within the locking aperture 348 when the needle 300 is disposed in the retracted position. The actuator button 360 is configured to cooperate with the locking aperture 348 in the rear barrel 344, to releasably engage the needle hub 340 with the rear barrel 344.

The needle 300 is operable between a projecting position illustrated in FIG. 3A and retracted position illustrated in FIG. 3B. In one example, the actuator button 360 allows a user to move the needle 300 from an extended position (FIG. 10) to a retracted position (FIG. 3B). A flat 362 of the actuator button 360 is engaged with a portion of the rear barrel 344 and retains the needle 300 in an extended position (FIG. 10). Once the actuator button 360 is depressed toward a longitudinal axis of the assembly 100, the flat 362 is released from the rear barrel 344, and the bias member 342 forces the needle 300 into a retracted position (FIG. 3B).

Figure 12:
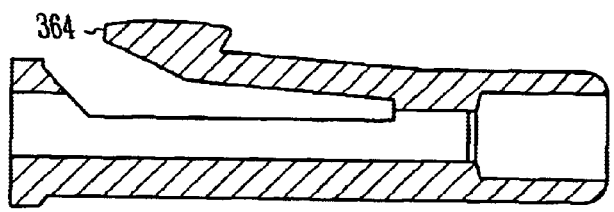
FIG. 12 illustrates a cross-sectional view of an actuator assembly constructed in accordance with one embodiment.

The assembly 300 optionally further provides for preventing re-extension of the needle 300 after retraction of the needle 300 within the dilator 120, so that a contaminated distal end 304 of the needle 300 is not exposed and cannot be reexposed. In one option, actuator 358 assists in preventing the re-extension of the needle 300, where the actuator 358 is shown in FIG. 12 in greater detail. The actuator button 360 includes a shoulder 364 that engages a flange 366 on an interior surface of the rear barrel 344, as shown in FIG. 10. As the needle 300 is retracted within the dilator 120, the needle retainer 346 moves past the flange 366, and flexes radially outwardly when it is displaced past the flange 366 and into the larger inner diameter 368. The shoulder 364 of the actuator button 360 abuts up against the flange 366 and prevents re-extension of the needle 300, if a user attempts to re-extend the needle 300.

Figure 4:
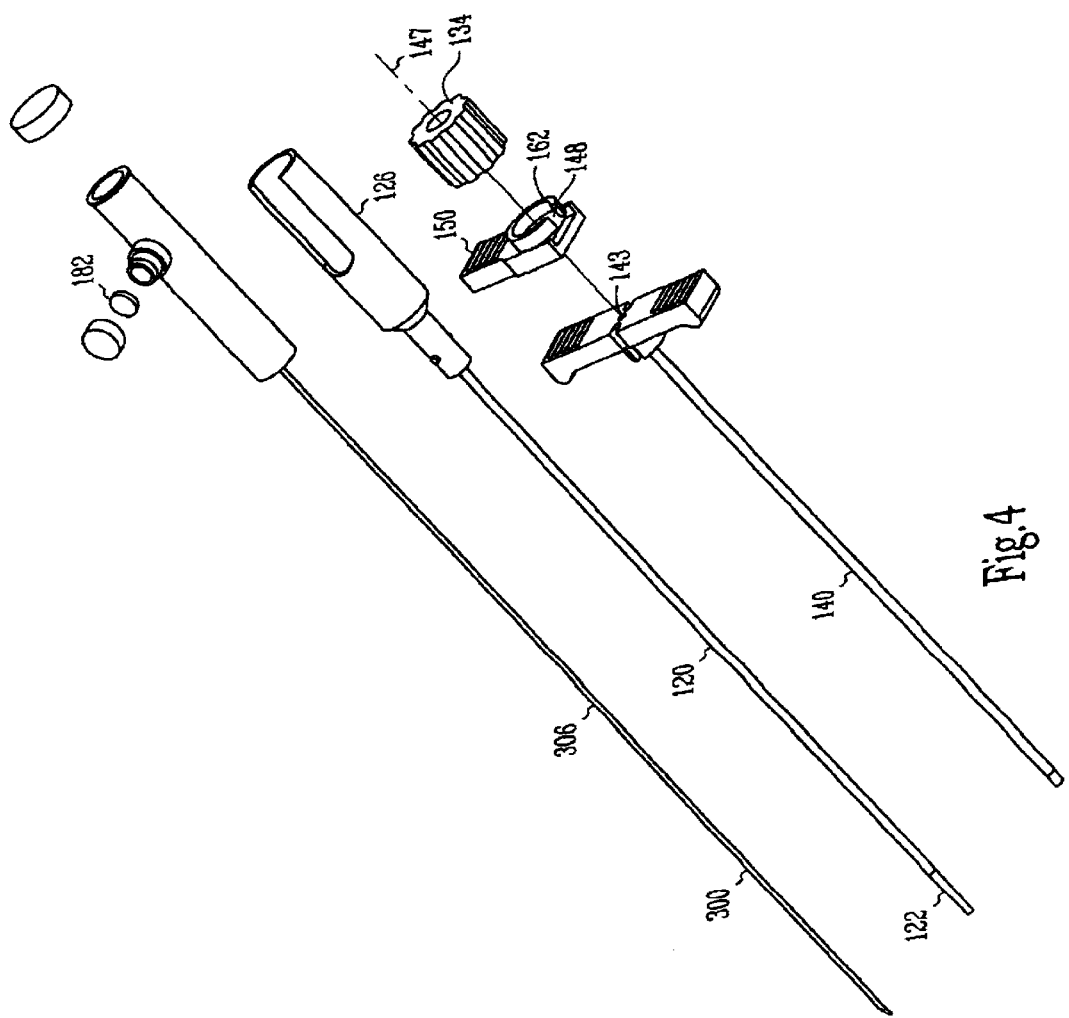
FIG. 4 illustrates a perspective view of a disassembled introducing apparatus as constructed in accordance with another embodiment.

In a further option, the sheath 140 includes a valve assembly 150 coupled therewith, as shown in more detail in FIGS. 4 and 5. Optionally, the valve assembly 150 is movably coupled with the at least one tab 210, where the valve assembly 150 is movable relative to a top surface 212 of the at least one tab 210. In another example, the valve assembly 150 is slidingly coupled with the at least one tab 210.

The valve assembly 150 includes a seal 152 and a valve support member 154. The valve support member 154, in combination with the seal 152, provide a hemostatic valve which seals against instruments which are disposed therethrough. In addition, the valve assembly 150 provides a seal for the passage 142 of the sheath 140, where little or no air is allowed to enter the vessel of a patient. The seal 152, in one option, comprises a membrane. A further option is that the seal 152 includes a slitted portion 156 therein. The slitted portion 156 can includes, but is not limited to, a number of different options such as a slit, a partial slit, a line of weakness, or a perforated line. In yet another option, the seal 152 comprises multiple sealing components, for instance, which are disposed adjacent to one another.

The valve support member 154 retains the seal 152. In addition, the valve support member 154 is coupled with the sheath 140, and allows for the valve assembly 150 to move relative to the sheath 140. The valve assembly 150 moves relative to the sheath in many different manners.

Figure 6:
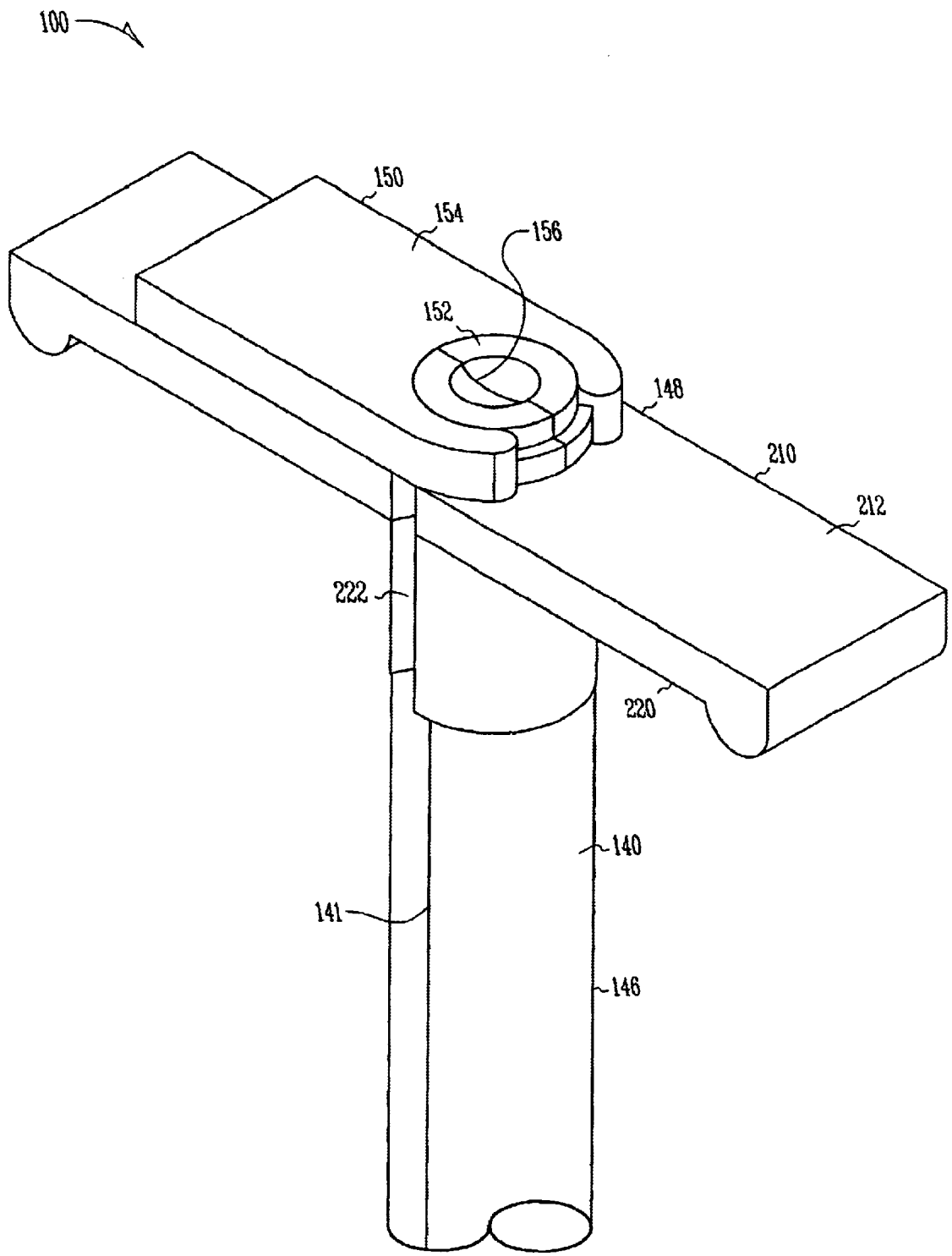
FIG. 6 illustrates a perspective view of a portion of an introducing apparatus as constructed in accordance with one embodiment.

In one example, the valve support member 154 is adapted to slide along a longitudinal axis of the at least one tab. The valve support member 154, in one option, is disposed around only a portion of the seal 152. In another option, the valve support member 154 flexes as an instrument is disposed through the seal 152. The movable valve assembly 150 is adapted to slide from a first position, as shown in FIG. 5, to a second position, as shown in FIG. 6. In the first position, the movable valve assembly 150 is disposed through the longitudinal axis of the sheath, sealing the passage of the sheath 140. In the second position, the movable valve assembly 150 is disposed away from the longitudinal axis of the sheath.

In another example, the movable valve assembly 150 is adapted to rotate about a hinge point on the at least one tab of the sheath. As the movable valve assembly 150 rotates, the valve assembly 150 slides on a top surface of the at least one tab. In another embodiment, the movable valve assembly 150 is adapted to rotate about a hinge point on the at least one tab. As the movable valve assembly 150 rotates about the hinge point, at least a portion of the valve assembly 150 is lifted away from the top surface of the at least one tab. The movable valve assembly 150 advantageously prevents blood from exiting the sheath 140 before or after a medical instrument has been inserted into the sheath 140. Instead of placing a thumb over the passage 143, or allowing blood to flow from the sheath 140, the physician moves the movable valve assembly 150 over the passage 143, and prevents blood from leaving the sheath 140.

Figure 7:
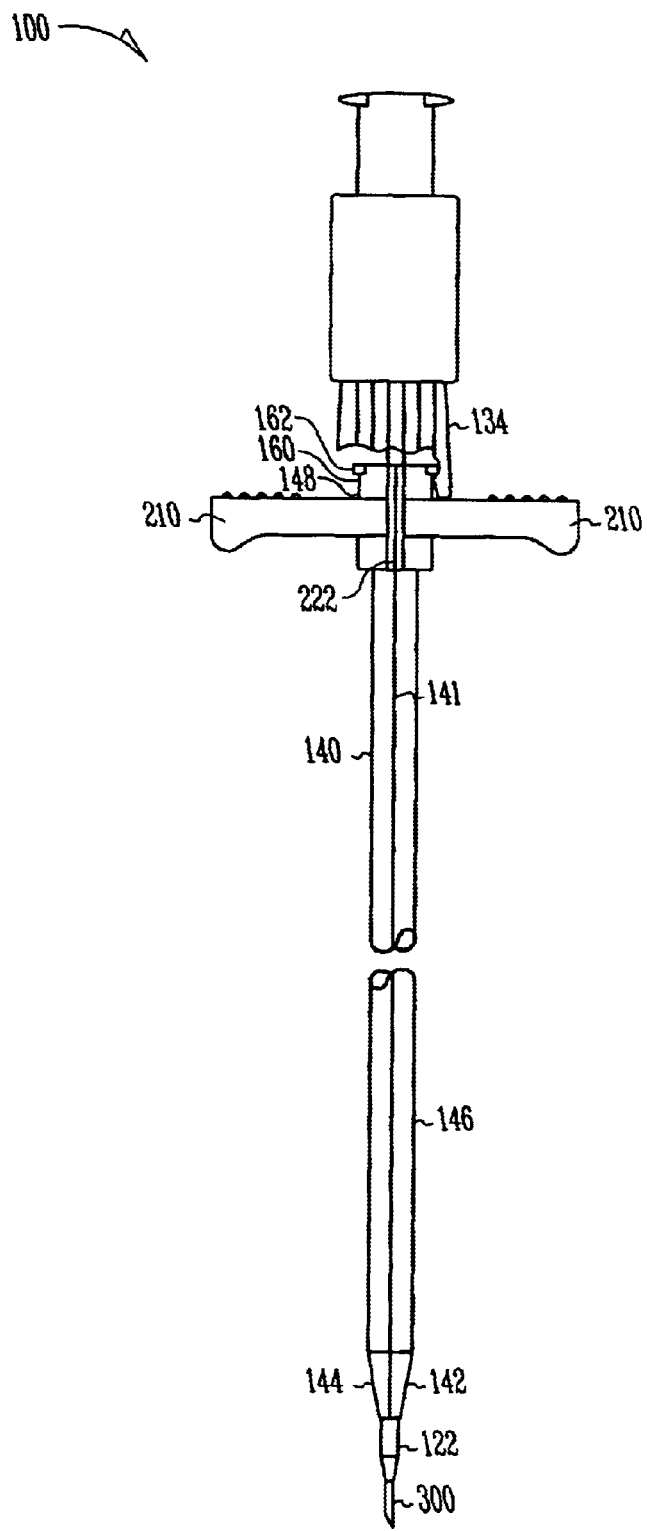
FIG. 7 illustrates a side elevational view of an introducing apparatus as constructed in accordance with one embodiment.

Referring to FIGS. 4 and 7, the sheath 140 optionally further includes locking features such that axial movement between the dilator 120 and sheath 140 is prevented, and optionally further includes anti-rotation features which prevent the dilator 120 from rotating relative to the sheath 140. The dilator 120 includes a rotatable fastener 134 (shown in a cut-away view) rotatably coupled therewith. The rotatable fastener 134 allows for coupling of the dilator 120 to the sheath 140 such that axial movement between the dilator 120 and sheath 140 is prevented. Optionally, the rotatable fastener 134 includes a threaded portion which threadingly engages with the lip 162 of the sheath hub 160.

The dilator 120 optionally includes anti-rotation features, as discussed in co-pending application Ser. No. 09/540,712 entitled "Locking Catheter Introducing System" filed on Mar. 31, 2000, and incorporated by reference herein. The anti-rotation features resist and optionally prevent the dilator 120 from rotating relative to the sheath 140. In addition, additional features allow for the anti-rotation features to be overcome, such that the user can selectively rotate the dilator 120 or can selectively lock the rotational movement of the dilator 120. The anti-rotation features, in one option, are disposed on a coupling portion of the dilator 120, and for example include a flat on the coupling portion of the dilator 120.

To assemble the introducing apparatus 100 of FIG. 4, the needle 300 is retractably coupled with the dilator 120. The distal end 122 of the dilator 120 is disposed within the sheath 140 until the dilator hub 126 is proximate to the proximal end 148 of the sheath 140. The rotatable fastener 134 is pressed against the lip 162 of the sheath 140 and the rotatable fastener 134 is rotated. As the fastener 134 is rotated, the dilator 120 becomes further inserted into the sheath 140, and becomes axially fixed to the sheath 140 as the threads engage the lip 162 of the sheath 140. In addition, as the fastener 134 is rotated, the anti-rotation features of the dilator 120 and/or the sheath 140 become seated such that further rotation of the rotatable fastener 134 does not cause rotation of the dilator 120 relative to the sheath 140, even when the fastener 134 is rotated to remove the axial fixation of the dilator 120 relative to the sheath 140.

During the implant process of the introducer assembly 100, the physician will stick the vessel with the needle and advance the needle and dilator into the vessel until the dilator distal end is about to enter the opening made by the needle. When the needle has entered the vessel, the pressure of the venous system will cause blood to flow up through the needle into the flash back chamber portion of the dilator hub, which allows the physician one way to visually confirm that the needle has entered the vessel. After verifying the vessel has been accessed by the needle, the dilator is advanced into the vessel. Since the needle is flexible, no guidewire is necessary as the dilator is directed through the vessel. Before, during, or after the dilator advancement through the vessel, the needle is retracted into the dilator. In one option, once the needle has been retracted, it can not be re-extended from the dilator. The physician optionally further advances the introducer assembly into the vessel. The dilator and retracted needle are removed from the sheath, leaving the sheath in the vessel. A medical device is implanted through the sheath and into the vessel of the patient. The sheath is removed from the medical device without damage to the vessel or the medical device by, for example, peeling or slitting the sheath with a tool.

Use of the apparatus, as described above and including the many variations, includes retractably coupling a needle with a dilator, the dilator extending to a dilator distal end, where the needle extends to a needle distal end and the needle distal end is more flexible than the dilator, and the needle distal end extends beyond the dilator distal end. The method further includes disposing the needle and dilator within a sheath to form an introducing apparatus, and inserting the introducing apparatus into a body.

Several options for the method are as follows. For example, in one option, the method further includes retracting the needle within the dilator, and removing the needle and the dilator from the sheath. In another option, the method further includes preventing re-extension of the needle from the dilator. In yet another option, the method further includes removing the dilator and needle from the sheath, inserting an instrument through the sheath, and separating the sheath from the instrument without damage to the instrument. A valve is coupled with the sheath in another option.

The present introducing assembly requires fewer parts, includes fewer steps than the traditional Seldinger Technique, and is less expensive to manufacture, and insert into a patient. A further benefit is that once the needle is retracted, the dilator cannot accidentally stick the implanter. In addition, the mechanism which prevents re-extension prevents the introducer used on one patient from being used on another patient. Since the guidewire is no longer necessary, fewer steps are needed to introduce an instrument into a patient, resulting in a faster process, and less trauma to a patient. Yet another advantage is that a more effective seal is made around the catheter or medical instrument since the device which retains or supports the valve flexes, for example, as instruments are inserted therethrough. The introducing assembly can be manufactured in a wide variety of sizes, and allows for any type of medical device or fluid to be disposed therethrough.

It is to be understood that the above description is intended to be illustrative, and not restrictive. Many other embodiments will be apparent to those of skill in the art upon reading and understanding the above description. It should be noted that embodiments or portions thereof discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. An introducing apparatus comprising:
   an elongate tubular sheath extending from a sheath proximal end to a sheath distal end, the sheath having a bore including an internal diameter sized to receive a dilator therethrough, the internal diameter sized to receive medial instruments therethrough;
   the dilator extending from a dilator proximal end to a dilator distal end;
   a needle disposed within the dilator, the needle extending from a needle proximal end to a needle distal end and including an intermediate portion therebetween, the intermediate portion is flexible;
   the needle distal end extending out of the dilator distal end in a first position, the needle distal end retracted within the dilator distal end in a second position; and
   a needle retraction mechanism coupled with the needle and the dilator, and the needle is retractably coupled with the dilator.

2. The introducing apparatus as recited in claim 1, wherein the sheath is separable without damage to an instrument inserted therethrough.

3. The introducing apparatus as recited in claim 1, wherein the needle distal end is more flexible than the dilator.

4. The introducing apparatus as recited in claim 1, wherein the needle distal end has the same or more flexibility as the dilator.

5. The introducing apparatus as recited in claim 1, wherein the intermediate portion of the needle comprises a flexible coil.

6. The introducing apparatus as recited in claim 1, wherein the intermediate portion and the needle distal end are flexible, and the intermediate portion and the needle distal end are formed of a unitary structure of nitinol.

7. The introducing apparatus as recited in claim 1, further including a gas permeable filter coupled with the dilator.

8. The introducing apparatus as recited in claim 1, wherein the needle proximal end includes a member sized and shaped to prevent re-extension of the needle.

9. The introducing apparatus as recited in claim 1, further comprising a locking mechanism configured to temporarily lock the sheath with the dilator.

10. The introducing apparatus as recited in claim 1, wherein the dilator further includes a blood flashback chamber.

11. The introducing apparatus as recited in claim 1, wherein an intermediate portion of the dilator is further defined by first and second dilator intermediate portions, the dilator first intermediate portion having a greater outer diameter than an outer diameter of the dilator distal end, the dilator second intermediate portion having a greater outer diameter than the outer diameter of the first intermediate portion.

12. The introducing apparatus as recited in claim 1, wherein the needle distal end is echogenic.

13. The introducing apparatus as recited in claim 1, further including a valve coupled with the sheath.

14. The introducing apparatus as recited in claim 13, wherein the valve comprises a sliding valve assembly slidingly engaged with a tab of the sheath, the sliding valve adapted to slide from a first position to a second position, in the first position the sliding valve disposed through the longitudinal axis of the sheath, in the second position the sliding valve disposed away from the longitudinal axis of the sheath.

15. The introducing apparatus as recited in claim 14, wherein the sliding valve assembly includes a membrane coupled with a sliding member.

16. An introducing apparatus comprising:
   an elongate tubular sheath extending from a sheath proximal end to a sheath distal end, the sheath having a bore including an internal diameter sized to receive a dilator therethrough;
   the sheath including at least one tab extending away from a longitudinal axis of the sheath;
   the dilator extending from a dilator proximal end to a dilator distal end;
   a needle disposed within the dilator, the needle extending from a needle proximal end to a needle distal end and including an intermediate portion therebetween, at least the needle distal end is flexible;
   the needle distal end extending out of the dilator distal end in a first position, the needle distal end retracted within the dilator distal end in a second position; and
   a needle retraction mechanism coupled with the needle and the dilator, and the needle is retractably coupled with the dilator.

17. The introducing apparatus as recited in claim 16, wherein the needle includes a catch sized and shaped to prevent extension of the distal end of the needle from the dilator distal end.

18. The introducing apparatus as recited in claim 16, wherein the sheath is separable without damage to an instrument inserted therethrough.

19. The introducing apparatus as recited in claim 16, wherein the needle distal end is more flexible than the dilator.

20. The introducing apparatus as recited in claim 16, wherein the dilator further includes a blood flashback chamber and a gas permeable filter.

21. The introducing apparatus as recited in claim 16, wherein an intermediate portion of the dilator is further defined by first and second dilator intermediate portions, the dilator first intermediate portion having a greater outer diameter than an outer diameter of the dilator distal end, the dilator second intermediate portion having a greater outer diameter than the outer diameter of the first intermediate portion.

22. The introducing apparatus as recited in claim 16, wherein the needle distal end is echogenic.

23. The introducing apparatus as recited in claim 16, further including a valve coupled with the sheath.

24. The introducing apparatus as recited in claim 23, wherein the valve comprises a sliding valve assembly slidingly engaged with the at least one tab, the sliding valve adapted to slide from a first position to a second position, in the first position the sliding valve disposed through the longitudinal axis of the sheath, in the second position the sliding valve disposed away from the longitudinal axis of the sheath.

25. A method comprising:
   disposing a needle within a dilator,
   retractably coupling said needle with said dilator, the dilator extending to a dilator distal end, where the needle extends to a needle distal end and the needle distal end is more flexible than the dilator, and the needle distal end extends beyond the dilator distal end;
   disposing the needle and dilator within a sheath to form an introducing apparatus; and
   inserting the introducing apparatus into a body.

26. The method as recited in claim 25, further comprising retracting the needle within the dilator, and removing the needle and the dilator from the sheath.

27. The method as recited in claim 26, further comprising preventing re-extension of the needle from the dilator.

28. The method as recited in claim 25, further comprising removing the dilator and needle from the sheath, inserting an instrument through the sheath, and separating the sheath from the instrument without damage to the instrument.

29. The method as recited in claim 25, further comprising coupling a valve with the sheath.

30. The method as recited in claim 25, further comprising coupling a coil between a position adjacent to the needle distal end and a needle proximal end to form a flexible portion therebetween.

* * * * *